(12) United States Patent
Levy et al.

(10) Patent No.: US 12,115,321 B2
(45) Date of Patent: Oct. 15, 2024

(54) PROTECTIVE SECUREMENT DEVICE

(71) Applicant: Mighty Well, Inc., Newport, RI (US)

(72) Inventors: Emily Ana Levy, Providence, RI (US); Yousef Al-Humaidhi, Providence, RI (US); Maria Del Mar Gomez Viyella, Providence, RI (US); Caitlin Allen, Bristol, RI (US)

(73) Assignee: Mighty Well, Inc., Newport, RI (US)

( * ) Notice: Subject to any disclaimer, the term of this patent is extended or adjusted under 35 U.S.C. 154(b) by 99 days.

(21) Appl. No.: 17/531,718

(22) Filed: Nov. 20, 2021

(65) Prior Publication Data

US 2022/0161001 A1    May 26, 2022

Related U.S. Application Data

(60) Provisional application No. 63/117,765, filed on Nov. 24, 2020.

(51) Int. Cl.
*A61M 25/01* (2006.01)
*A61M 25/02* (2006.01)
*A61B 46/23* (2016.01)
*A61B 46/27* (2016.01)

(52) U.S. Cl.
CPC ....... *A61M 25/02* (2013.01); *A61B 2046/234* (2016.02); *A61B 46/27* (2016.02); *A61M 2025/0213* (2013.01); *A61M 2025/0246* (2013.01); *A61M 2025/0253* (2013.01); *A61M 2025/026* (2013.01)

(58) Field of Classification Search
CPC .......... A61M 25/02; A61M 2025/0246; A61M 2025/0213; A61M 2025/0253; A61M 2025/026; A61M 2025/0206; A61B 46/27; A61B 2046/234; A61F 2013/00093
See application file for complete search history.

(56) References Cited

U.S. PATENT DOCUMENTS

| 4,799,923 | A | * | 1/1989 | Campbell | A61M 25/02 604/179 |
|---|---|---|---|---|---|
| 5,823,977 | A | | 10/1998 | Dalyea | |
| 6,276,364 | B1 | | 8/2001 | Warner | |
| D818,120 | S | | 5/2018 | Levy et al. | |
| 10,285,842 | B2 | * | 5/2019 | Hodges, IV | A61F 5/0106 |
| 2016/0213885 | A1 | * | 7/2016 | Carlson | A61M 25/02 |
| 2018/0015258 | A1 | * | 1/2018 | Shen | A61M 25/02 |

* cited by examiner

*Primary Examiner* — Nathan R Price
*Assistant Examiner* — Tania Ismail
(74) *Attorney, Agent, or Firm* — Hinckley, Allen & Snyder LLP; David R. Josephs

(57) ABSTRACT

The present disclosure is directed to a device that can be in the form of a sleeve that has a first upper portion and a second lower portion. The first upper portion can include exit ports to allow various catheters, such as peripherally inserted central catheter (PICC) lines, to extend through openings therein. The second lower portion is inverted upwardly over the first portion and can have a securement flap on an outer surface to tighten around the patient's arm and around the PICC line to ensure that the PICC line and the sleeve remain stationary relative to the patient's arm.

12 Claims, 2 Drawing Sheets

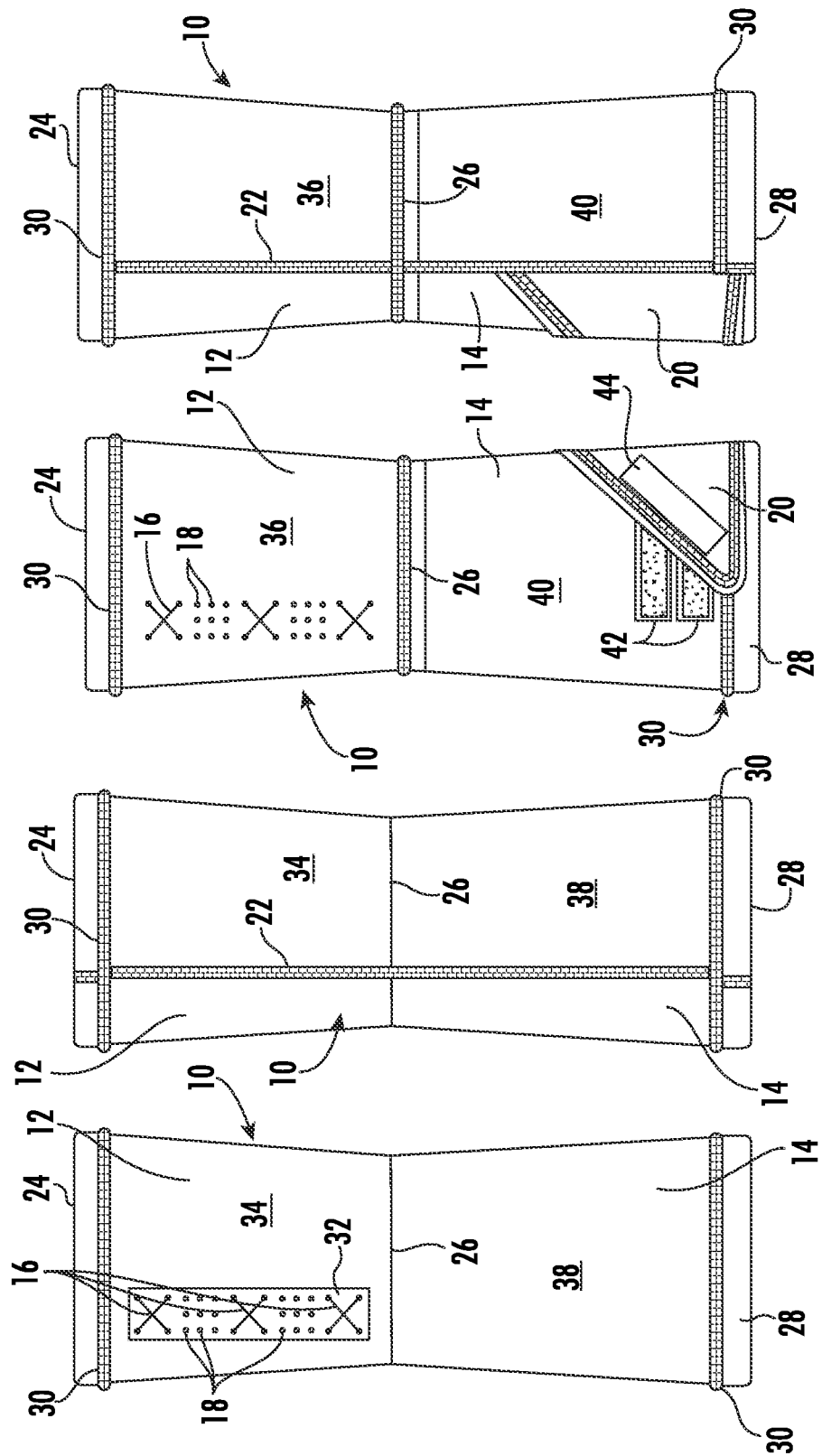

PROTECTIVE SECUREMENT DEVICE

CROSS REFERENCE TO RELATED APPLICATIONS

This application is related to and claims priority from earlier filed U.S. Provisional Patent Application No. 63/117,765, filed Nov. 24, 2020, the entirety thereof is incorporated herein by reference.

BACKGROUND OF THE INVENTION

The present disclosure generally relates to a protective device for a catheter inserted in a patient's arm. More specifically, the present disclosure relates to a securement sleeve worn by a patient to cover and protect a catheter line, such as peripherally inserted central catheter (PICC) line or midline catheter line, inserted in a patient's upper arm.

In the medical industry, intravenous or IV therapy involves the administration of liquids directly into a patient's veins through an inserted catheter. Long-term, continuous IV therapy (for administrating chemotherapy regimens, frequent drawing of blood samples, antibiotic regimens, or parenteral nutrition) is usually accomplished with a peripherally inserted central catheter (PICC) line. Accordingly, patients suffering from various medical diagnoses may require a PICC line to be inserted into the vein of the patient's upper arm, during a hospital stay.

A PICC is often a small, soft tube that is placed in a vein in a patient's upper arm. A PICC line is often employed when a treatment requires the administration of medicines or nutrition for weeks or months at a time. Thus, the clinician will leave the PICC in place to avoid having to insert a catheter each time vein access is required, which would compromise the vein. At home, patients are counseled that they need to take care of the PICC to keep it functioning properly. Because a PICC line has a high infection risk, a patient must take extra care washing hands and preventing the spread of germs near, or around, the insertion site. In addition to the aforementioned risks, another persistent problem is inadvertent pulling out of the PICC from the patient due to snagging, or other pulling of the port. This can result in undesirable catheter migration and/or catheter dislodgement. The re-insertion of the PICC line can be a painful procedure for the patient and costly for both the patient and the provider.

There have been attempts in the prior art to address the foregoing known problems in the industry. However, typically, the current solution for secondary protection of the catheter has been a sock or stockinette that is placed over the port. This solution is often unattractive and draws attention to a medical condition that a patient may want to avoid. Additionally, the sock does not adequately protect the PICC line as the line still has to exit out the top of the sock. Moreover, a sock may not be sufficiently tight to stay in the correct place on the user's arm. Still further, socks are commonly made of thick fabrics that undesirably prevent breathability around the insertion site.

Prior art devices have only a single layer, which is not sufficient to secure the catheter lines or prevent catheter migration for patients. Moreover, this single-layer design does not adequately prevent the catheter from being in contact with the patient's skin, which often causes irritation. In addition, prior art devices are devoid of an adjustment mechanism, making it impossible to customize them for a secure and comfortable fit.

For the foregoing reasons, there is a need for a protective device for a catheter inserted in a patient's arm. There is a further need for a securement sleeve worn by a patient to cover and protect a PICC line inserted in a patient's upper arm. There is a still further need for an aesthetically pleasing, adjustable securement sleeve worn by a patient to cover and protect a peripherally inserted central catheter (PICC) line inserted in a patient's upper arm.

SUMMARY OF THE INVENTION

In this regard, the present disclosure provides for a protective device for a catheter, or the like, inserted in a patient's arm. The disclosed securement sleeve is worn by a patient to cover and protect an inserted catheter, such as a peripherally inserted central catheter (PICC) line inserted in a patient's upper arm or midline catheter. For ease of discussion, a PICC line is discussed in detail herein but it should be understood that the present invention is related to and can be used with any type of catheter.

In general, the device, or securement device, as disclosed can be in the form of a sleeve that has a first upper portion and a second lower portion. The first upper portion can include exit ports, or exit points, to allow various PICC lines, or other medical tubing, to extend therethrough. The first upper portion can additionally include a plurality of openings to allow for breathability around the insertion site. The second lower portion can have a securement flap, or strap, on an outer surface to tighten around the user's appendage, or arm, and around the PICC line to ensure that the PICC line is secured, and the sleeve remains stationary relative to the user's arm. Once secured to the user's arm, the PICC line can be secured in between the first upper portion and the second lower portion. The resulting protective device is an aesthetically pleasing protective option to keep the external part of the PICC secured and prevent a PICC line from being inadvertently pulled out due to patient activity.

It is therefore an object of the present disclosure to provide a protective device for a catheter inserted into the body of a patient, such as a patient's arm. It is a further object to provide a securement sleeve worn by a patient to cover and protect a PICC line inserted in a patient's upper arm. This helps prevent the catheter from being inadvertently pulled due to the patient's daily activities. Still further the present disclosure provides an aesthetically pleasing, adjustable securement sleeve worn by a patient to cover and protect a peripherally inserted central catheter (PICC) line inserted in a patient's upper arm.

These together with other objects of the disclosure, along with various features of novelty which characterize the disclosure, are pointed out with particularity in the claims annexed hereto and forming a part of this disclosure. For a better understanding of the disclosure, its operating advantages, and the specific objects attained by its uses, reference should be had to the accompanying drawings and descriptive matter in which there is illustrated a preferred embodiment of the invention.

BRIEF DESCRIPTION OF THE DRAWING FIGURES

The novel features that are characteristic of the present disclosure are set forth in the appended claims. However, the disclosure's preferred embodiments, together with further objects and attendant advantages, will be best understood by reference to the following detailed description taken in connection with the accompanying drawings in which:

FIG. 1A is a front view of the outer surface of a protective sleeve according to a first embodiment;

FIG. 1B is a rear view of the outer surface of the protective securement device of FIG. 1A;

FIGS. 2A & 2B are views of the protective securement device of FIG. 1A turned inside out.

DESCRIPTION OF THE INVENTION

Figure 3C:
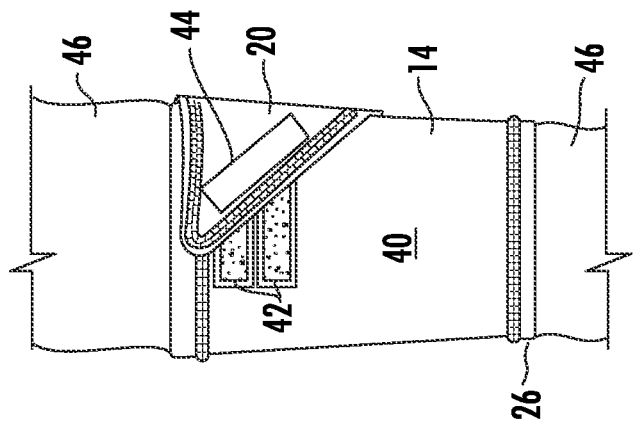
FIGS. 3A, 3B and 3C are a sequence showing the installation of the protective sleeve on a patient's arm.

Certain exemplary embodiments will now be described to provide an overall understanding of the principles of the structure, function, manufacture, and use of the device and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present disclosure. Further, in the present disclosure, like-numbered components of the embodiments generally have similar features, and thus within a particular embodiment, each feature of each like-numbered component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Further, to the extent that directional terms like proximal, distal, top, bottom, up, or down are used, they are not intended to limit the systems, devices, and methods disclosed herein. A person skilled in the art will recognize that these terms are merely relative to the system and device being discussed and are not universal. Further, while the below disclosure is described with respect to PICC lines, this protective sleeve can be used with any variety of other medical, or non-medical, devices.

In the prior art, it is well known to use a traditional sock, tubular stockinette bandage, or other gauze, that one would wear on their arm to secure a catheter, such as a PICC line, in place. A user will take a tube sock, or a sock of an acceptable length and cut the toe end off. Then the user will slide the sock up their arm to cover the PICC line. These solutions suffer from a number of shortcomings, including: 1) the sock or stockinette stretch out quickly and can be too loose which can result in a poor fit; 2) socks or stockinettes are not adjustable; 3) socks or stockinettes do not allow access to the PICC; 4) socks or stockinettes may snag, and therefore dislodge, the catheter; and 5) socks or stockinettes are unsanitary. Thus, the present disclosure provides advantages over the prior art by providing a sleeve that is adjustable to maintain a secure fit that won't slide to reliably keep the PICC line protected and secured.

Turning now to FIGS. 1A and 1B, the device 10, or securement device, can be in the form of a sleeve that has a first upper portion 12 and a second lower portion 14. The first upper portion 12 can include exit ports 16, or exit points, to allow various PICC lines, or other medical tubing, to extend therethrough. The first upper portion 12 can additionally include a plurality of vent openings 18 to allow for breathability of the patient's arm around the PICC insertion site. As can best be seen in FIGS. 2A and 2B, the second lower portion 14 can have a securement flap 20, or strap, on an outer surface to tighten around the user's appendage, or arm, and around the location of the inserted PICC line to ensure that the PICC line is secured and the securement device 10 remains stationary relative to the user's arm. Once secured to the user's arm, the PICC line can be secured in between the first upper portion 12 and the second lower portion 14. The resulting protective device is an aesthetically pleasing protective option to keep the external part of the PICC secured and prevent a PICC line from being inadvertently pulled out due to patient activity.

The first upper portion 12 and second lower portion 14 can be formed from a single tube of material. Alternatively, the securement device 10 can be stitched together from any number of pieces of material. The securement device 10 can be made of any suitable fabric including cotton, neoprene, other natural or synthetic materials, elastic materials, and/or antimicrobial materials (either impregnated or coated) including silver bromide and silver ions. The size of the securement device 10 can vary to accommodate any number of sized users. The securement device 10 of material can have a central stitch 22 that extends parallel to a central axis of the securement device 10 to create the tubular shape.

In a first, unfolded configuration of the securement device 10, when laid flat on a surface the securement device 10 can have an angular hourglass shape formed from two trapezoids e.g., the first upper portion 12 and the second lower portion 14. When the securement device 10 is worn around a user's arm, in an unfolded configuration, can have an opposing frustoconical shape. In the first unfolded configuration, the proximal-most edge 24 of the securement device 10 can have a first diameter that tapers towards a center 26, or midline, of the securement device 10. The securement device 10 can have a second diameter at the midline 26. The second diameter at the midline 26 can be smaller than the first diameter at the proximal edge 24. Extending down from the center, or midline 26, of the securement device 10 is the second lower portion 14 that can flare outward to the distal most end 28 of the securement device 10. The distal most end 28 can have a third diameter that is substantially the same diameter as the first diameter at the proximal end 24. When the securement device 10 is disposed on a user's arm, the first diameter, as well as the third diameter, can be larger to be fit over the user's bicep and second diameter can be smaller to conform to the area above the elbow thereby assisting in maintaining the position of the securement device 10 on the patient's arm. The securement device 10 can have a folded finish at the proximal-most edge 24 and distal 28 ends of the securement device 10 to create a clean finish with a flatlock cover-stitch 30, though other finishes are encompassed by this disclosure.

The first upper portion 12 can include an axially running strip of material 32, running parallel to the central axis of the securement device 10, that includes a plurality of exit ports 16 and laser cut openings 18, or breathing holes. The exit ports 16 can be, as shown, in the form of X-shaped openings. The breathing holes 18 can provide for breathability around the PICC line insertion site. The strip of material 32 can be stitched on to an outer surface 34 of the first upper portion 12, as depicted in FIGS. 1A and 1B where the securement device 10 is shown right side out, or on an interior surface 36 as depicted in FIGS. 2A and 2B where the securement device 10 is shown inside out. For the sake of clarity, the inner surface 36 of the first upper portion 14 is understood to be the surface of the securement device 10 that is in contact with the user's arm when worn, and the outer surface 34 is the opposite surface. The additional strip of material 32 can be the same material as the securement device 10 or can be made of another material e.g. a BEMIS overlay film. In the illustrated embodiment there are three exit ports 16, but there can be only one exit port or more than three exit ports depending on the medical needs of the user. Additionally, or alternatively, the strip of material 32 can include any number of laser cut openings 18 to allow for air flow and visibility around the PICC line insertion point to aid in infection prevention.

The second lower portion 14 can have an inner surface 40 and an outer surface 38. In this case, the inner surface 40 when the securement device 10 is extended, unfolded and flat. When the second lower portion 14 is folded upward and over the upper portion 12, during use, the outer surface 38 of the second lower portion 14 is facing inward and in at least partial contact with the outer surface 34 of the first upper portion 12. Similarly, the inner surface 40 of the second lower portion 14 is then outward facing when the second lower portion 14 is folded upward. The inner surface 40 of the second lower portion 14 can include at least one strip 42 of either a hook or loop material, of the hook and loop fastener. In the illustrated embodiment, there are two strips 42 of hook material running perpendicular to the central axis of the securement device 10. The inner surface 40 of the second lower portion 14 additionally includes a strap 20, or flap, that extends tangentially from the inner surface 40 of the second lower portion 14 to wrap around the user's arm and the PICC lines to ensure a secure fit. In the illustrated embodiment, the strap 20 has a generally triangular shape and at least one corresponding strip 44 of hook or loop material on the face of the strap 20 that comes into contact with the strips 42 on the inner surface 40 of the second lower portion 14. The strap 20 can have other geometric shapes including rectangular. Importantly, if a hook and loop fastener is used, one of the hook and loop material is placed on the inner surface 40 of the second lower portion 14 and the other of the hook and loop is placed on the strap 20, e.g. the hook material is on the inner surface 40 of the second lower portion 14 and the loop material is on the strap 20 and vice versa.

Figure 3B:
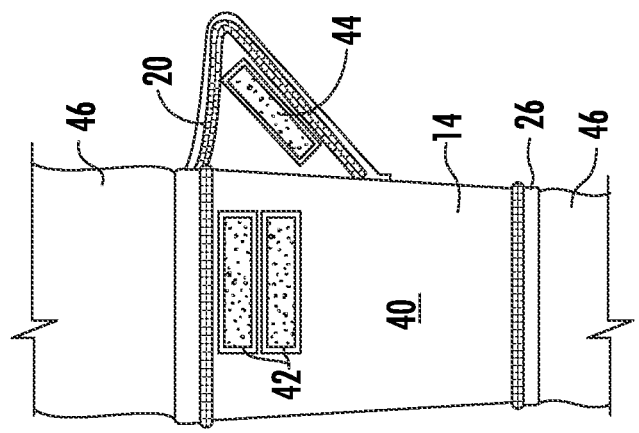
Figure 3A:
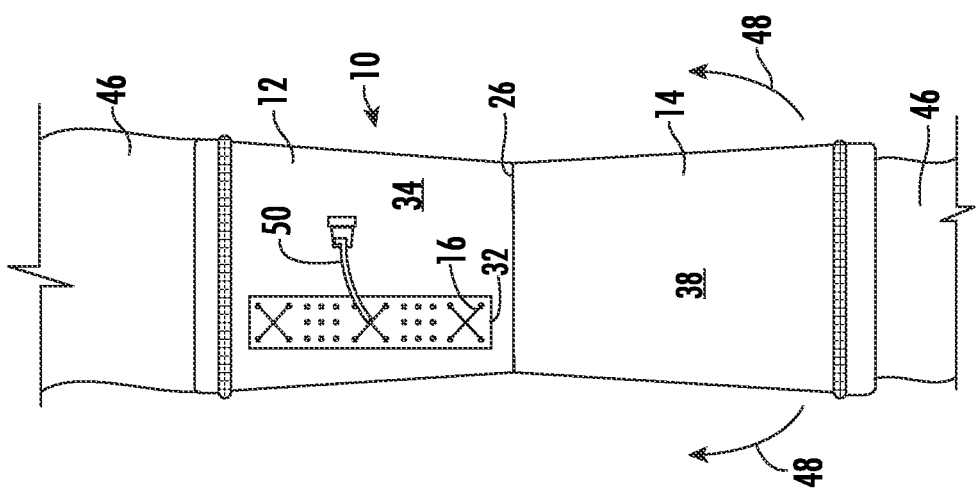

As best illustrated in FIGS. 3A, 3B and 3C, in use, the user inserts their arm 46 into the securement device 10 with the exit ports 16 arranged over the PICC line 50 inserted in the user's arm 46. The user can thread the PICC line 50 through any one of the exit ports 16 in the first upper portion 12. The second lower portion 14 is then "flipped" up and over as indicated by arrows 48 in FIG. 3A onto the first upper portion 12, about the mid-line 26 thereby locating the strap 20 outside for accessibility by the patient. As shown in FIG. 3B, the PICC line 50 is thus "trapped" between the outer surface 34 of the first upper portion 12 and the outer surface 38 of the second lower portion 14. The second lower portion 14 covers the exposed PICC 50 line to prevent the PICC line 50 from being pulled or snagged on any external structures. Then the strap 20, or securement flap, can be affixed as shown in FIG. 3C to the inner surface 40 such that the hook and loop strip 44 on the strap 20 comes into contact with the corresponding hook and loop strip 42 on the inner surface 40 of the lower portion 14 to tighten and adjustably secure the assembly around the user's arm 46 to prevent the securement device 10 from sliding down the user's arm 46. Such a strap is a great improvement over prior art PICC line sleeves in that it better secures the sleeve in place compared to prior art devices and is more customizable for superior comfort for the patient.

It should also be understood that the device 10 of the present invention can be provided and configured in any desired size to accommodate a given patient's arm 46. For example the length, circumference and overall shape of the device may be modified and still be within the scope of the present invention. Also, the number and size of the ports 16 may be modified to suit the needs of a patient. Further, the materials of the device discussed above are preferred but can be changed and still be within the scope of the present invention.

It will be appreciated by those skilled in the art that various changes and modifications can be made to the illustrated embodiments without departing from the spirit of the present disclosure. All such modifications and changes are intended to be covered by the appended claims.

What is claimed is:

1. A protective device, comprising:
a tubular upper portion;
a tubular lower portion having a surface; the lower portion being connected to the upper portion at a center midline between the upper portion and the lower portion; a mechanical fastener on the surface of the tubular lower portion;
at least two exit ports extending through a wall of the upper portion;
a flap, having an attachment edge and a flap surface facing the surface of the lower portion, extending laterally outward from the lower portion and connected to the surface of the lower portion via the attachment edge, a mechanical fastener located on the flap surface, wherein the flap extends from the surface of the lower portion and is hingedly connected to the surface of the lower portion, the mechanical fastener on the flap surface being releasably and adjustably secured to the mechanical fastener on the surface of the lower portion;
wherein the upper portion is configured and arranged to be positioned on a user's appendage;
a catheter line configured and arranged to be inserted into the user's appendage and extending through one of the at least two exit ports;
wherein the lower portion is configured and arranged to be invertible up and over the upper portion in a direction in line with the user's appendage thereby exposing the surface of the lower portion and the flap connected thereto; the catheter line being located between the upper portion and the lower portion;
wherein the flap is configured and arranged to tighten and secure the protective device in a transverse direction to maintain the catheter line in a captured position.

2. The protective device of claim 1, wherein the upper portion and the lower portion are constructed of one piece of material.

3. The protective device of claim 1, wherein the upper portion and the lower portion are separate pieces of material fastened to one another at the center midline.

4. The protective device of claim 1, wherein the tubular upper portion and the tubular lower portion are both frustoconical with their respective narrower dimension meeting at the center midline.

5. A method of protecting a catheter line inserted in a user's body, comprising the steps of:
placing a protective device over a catheter line configured and arranged to be in a user's appendage, the protective device comprising:

an upper portion;
a lower portion having a surface with a mechanical fastener thereon; the lower portion being connected to the upper portion at a center midline;
at least two exit ports extending through a wall of the upper portion; and
a flap having an attachment edge and a flap surface facing the surface of the lower portion extending laterally outward from the lower portion and connected to the surface of the lower portion via the attachment edge, the flap including a mechanical fastener on the flap surface;
    the flap extending from the surface of the lower portion and is hingedly connected to the surface of the lower portion; the mechanical fastener on the flap surface being releasably and adjustably secured to the mechanical fastener on the surface of the lower portion;
inserting a free end of the catheter line through one of the at least two exit ports;
inverting the lower portion up and over the upper portion; and
tightening the protective device with the flap in a transverse direction, the device being configured and arranged about the user's appendage and catheter line therein.

6. The method of claim 5, wherein the upper portion and the lower portion are constructed of one piece of material.

7. The method of claim 5, wherein the upper portion and the lower portion are separate pieces of material fastened to one another at the center midline.

8. The method of claim 5, wherein the upper portion and the lower portion are both tubular.

9. The method of claim 5, wherein the upper portion and the lower portion are both frustoconical with their respective narrower dimension meeting at the center midline.

10. The method of claim 5, wherein the at least two exit ports are three exit ports.

11. The method of claim 5, wherein the flap extends from an interior surface of the lower portion such that the interior surface and the flap are exposed when the lower portion is inverted up and over the upper portion.

12. The method of claim 11, further comprising the steps of:
    capturing the catheter line between the inverted lower portion and the upper portion,
    fastening the flap to tighten the protective device and secure it in a closed position.

\* \* \* \* \*